United States Patent [19]

Pemberton

[11] 4,000,136
[45] Dec. 28, 1976

[54] STABILIZED (THIO) PHOSPHATE COMPOSITIONS

[75] Inventor: Denis Pemberton, Manchester, England

[73] Assignee: Imperial Chemical Industries Limited, London, England

[22] Filed: Aug. 14, 1974

[21] Appl. No.: 497,513

[30] Foreign Application Priority Data

Aug. 31, 1973 United Kingdom ............ 41020/73

[52] U.S. Cl. .................... 260/251 P; 260/256.4 E; 260/256.5 R; 260/989
[51] Int. Cl.$^2$ .................. C07F 9/09; C07D 239/00
[58] Field of Search ........ 260/256.4 E, 989, 251 P, 260/256.5 R

[56] References Cited
UNITED STATES PATENTS 3,439,068  4/1969  Hill et al. ...................... 260/989 X

*Primary Examiner*—Anton H. Sutto
*Attorney, Agent, or Firm*—Cushman, Darby & Cushman

[57] ABSTRACT

Esters of an acid or thioacid of phosphorus stabilized by the calcium, magnesium, zinc or especially aluminium chelate of β-dicarbonyl compounds, in particular, acetyl acetone. Particularly valuable for pesticidal esters such as those of 4-hydroxypyrimidine. Stabilization is often better than that achieved with conventional stabilizers such as epoxides especially with phosphate esters.

9 Claims, No Drawings

STABILIZED (THIO) PHOSPHATE COMPOSITIONS

This invention relates to stabilised compositions containing esters of acids of phosphorus.

Esters of acids and thioacids of phosphorus are used as stabilisers for polymers, additives to lubricants and fuels, flameproofing agents, antistatic agents and as pesticides. These esters are in many cases unstable to storage, often especially if exposed to light. It has now been found that the stability of these esters can be significantly increased by the addition of certain metal chelate compounds.

According to the invention there are provided stabilised compositions comprising an ester of an acid or thioacid of phosphorus and a chelate compound of aluminum, calcium, magnesium or zinc with a compound of the formula:

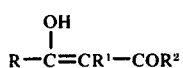

wherein $R^1$ is a hydrogen atom or an optionally substituted alkyl, aryl or aralkyl group, R is a group of the type $R^1$ or an alkoxy group or together with the group $R^1$ and the carbon atoms joining them forms a carbocyclic ring, and $R^2$ is a group of the type $R^1$ or an alkoxy group.

The acid or thioacid of phosphorus may be an acid of trivalent phosphorus or pentavalent phosphorus, for example phosphorous, phosphonic and phosphinic acids and orthophosphoric and pyrophosphoric acids, or an acid derived from any of these by replacement of one or more of the oxygen atoms by sulphur atoms as for example in thiophosphorous acid, thiophosphoric acid or dithiophosphoric acid.

Each esterifying group may be an alcohol, phenol or especially heterocyclic hydroxylic compound such as 4-hydroxypyrimidyl compounds or substituted derivative thereof. The ester of the acid or thioacid of phosphorus may contain two or more different esterifying groups.

As examples of esters of acids of phosphorus which may give the stabilised compositions of the invention there are mentioned diethyl 2-diethylamino-6-methylpyrimidin-4-yl phosphate and dimethyl 2,2-dichlorovinyl phosphate.

As examples of esters of thioacids of phosphorus which may give the stabilised compositions of the invention there are mentioned especially esters used for pesticidal purposes such as O,O-diethyl 2-N-ethylacetamido-6-methylpyrimidin-4-yl phosphorothionate and similar compounds disclosed in our copending application No. 13477/71, O,O-diethyl 2-dimethylamino-6-methylpyrimidin-4-yl phosphorothionate and similar compounds disclosed in British patent specification Nos. 1,019,227 and 1,203,026, O,O-diethyl-2-diethylamino-6-methylpyrimidin-4-yl phosphorothionate disclosed in our British patent specification No. 1,205,000, and O,O-dimethyl 2-diethylamino-6-methylpyrimidin-4-yl phosphorothionate disclosed in our British patent specification No. 1,204,552, and esters of thioacids of phosphorus disclosed in British patent specification No. 1,278,162.

As compounds which will form the chelate compound used in the compositions of the invention there are mentioned for example alkyl salicylates, such as ethyl salicylate, and also β-dicarbonyl compounds of the formula $R-CO-CHR^1-CO-R^2$ which afford chelate compounds derived from the enolic form of the β-dicarbonyl compounds. The preferred β-dicarbonyl compounds are those in which R is a alkyl group containing from one to three carbon atoms, $R^1$ is a hydrogen atom and $R^2$ is an alkyl or alkoxy group containing from one to five carbon atoms, and in particular acetylacetone. As other β-dicarbonyl compounds there are mentioned propionylacetone, 3-ethylacetylacetone, ethyl acetoacetate, benzoylacetone and diethyl malonate.

The chelate compounds used in the compositions of the invention are well-known and may be prepared by conventional and well-known methods. The preferred chelate compounds are derived from aluminum.

The amount of chelate compound is preferably between 1 and 10% based on the weight of ester of the acid or thioacid of phosphorus. Less can be used but the effect on stability is not always significant and the use of more may have little further effect owing to limited solubility of the chelate compound. A convenient proportion of chelate compound is about 2% of the ester.

The stabilised compositions may consist essentially of only the ester of the acid or thioacid or phosphorus and the chelate compounds, but particular valuable stabilised compositions are pesticidal compositions consisting of solutions of the esters together with the chelate compound dissolved in solvents, especially aromatic and aliphatic hydrocarbons, optionally containing surface active agents, or of powders consisting of such esters and the chelate compound absorbed on inorganic or organic solids such as silica, talc, nut shell powders, or rice flours.

The stability afforded by the chelate compounds to esters of thioacids of phophorus is in general greater than that obtained by the use of known stabilisers such as epoxides. The superiority over epoxides, and other stabilisers to esters of phosphorus thioacids such as benzoquinone, is even more marked in esters of acids of phosphorus such as phosphates, in which these other stabilisers have little effect or may even increase decomposition. The compositions of the invention can however contain in addition these other stabilisers for example epoxides such as epichlorohydrin, cyclohexane epoxide or styrene epoxide.

The chelate compounds may be incorporated into the other components of the stabilised compositions by any conventional method, for example, mixing with or dissolving in the ester of the acid or thioacid of phosphorus or dissolving in a solution of the ester and then mixing with any other components of the composition.

The invention is illustrated but not limited by the following examples in which all parts and percentages are by weight unless otherwise stated.

EXAMPLE 1

One part of O,O-dimethyl-2-diethylamino-6-methylpyrimidin-4-yl phosphorothionate and the listed amount of additive are mixed in a sealed glass tube and immersed in a bath at 80° C for 32 hours. The percentage decomposition of the ester of thioacid of phosphorus is then found by determining the gas-liquid chromatography the content of ester in the mixture. The results are as follows:

| Stabiliser | % of Stabiliser | % Decomposition |
| --- | --- | --- |
| None | — | 32 |
| Aluminium tris (acetylacetonate) | 2.0 | 15 |
| Aluminium tris-(1-carbethoxyacetonate) | 2.0 | 17 |
| Aluminium tris-(3-ethyl-acetylacetonate) | 2.0 | 20 |
| Aluminium tris-(propionylacetonate) | 2.0 | 18 |

EXAMPLE 2

The procedure of Example 1 is repeated with the stabilisers listed below, using a different sample of ester, for 5 days at 80° C.

| Stabiliser | % of Stabiliser | % Decomposition |
| --- | --- | --- |
| None | — | 59 |
| Calcium bis (acetylacetonate) | 2.0 | 43 |
| Magnesium bis (acetylactonate) | 2.0 | 26 |
| Zinc bis (acetylacetonate) | 2.0 | 35 |

EXAMPLE 3

The procedure of Example 1 is repeated with the stabilisers listed below, for 10 days at 80° C, using a 40% solution of the ester with 4% of calcium dodecylbenzenesulphonate in a commercially available mixture of alkylbenzenes.

| Stabiliser | % of Stabiliser | % Decomposition |
| --- | --- | --- |
| None | — | 42 |
| Aluminium tris (acetylacetonate) | 2.0 | 15 |
| Magnesium tris (acetylacetonate) | 2.0 | 32 |

EXAMPLE 4

The procedure of Example 1 is repeated with the stabilisers listed below using diethyl-2-diethylamino-6-methylpyrimidin-4-yl phosphate as the ester of acid of phosphorus at a temperature of 80° C for 11 days.

| Stabiliser | % of Stabiliser | % Decomposition |
| --- | --- | --- |
| None | — | 4.2 |
| Aluminium tris (acetylacetonate) | 2.0 | 1.3 |
| Epichlorohydrin | 5.0 | 5.7 |
| p-Benzoquinone | 2.0 | 23.0 |

EXAMPLE 5

The stabilisers listed below were added to diethyl-2-diethylamino-6-methylpyrimidin-4-yl phosphate and a portion of each sample was stored in a clear glass bottle exposed to daylight for ten months at room temperature. The percentage decomposition was then determined by gas-liquid chromatographic analysis.

| Stabiliser | % of Stabiliser | % Decomposition |
| --- | --- | --- |
| None | — | 13 |
| Aluminium tris (acetylacetonate) | 2.0 | 0 |
| Epichlorohydrin | 5.0 | 8 |
| Benzoquinone | 2.0 | 11 |

EXAMPLE 6

A 40% solution of dimethyl-2,2-dichlorovinyl phosphate in a commercially available mixture of alkylbenzenes is stored for 5 days at 75° C. The percentage decomposition of the phosphoric ester over this time is found to be 78%. Under the same storage conditions a sample of the same solution to which 2% (based on the weight of ester) of aluminum tris(acetylacetonate) has been added is found to have decomposed by 28%.

EXAMPLE 7

The procedure of Example 1 is repeated with the stabilisers listed below, for 3 days at 70° C, using dimethyl-2,2-dichlorovinylphosphate as the ester of acid of phosphorus in 20% solution in a commercially available mixture of alkylbenzenes.

| Stabiliser | % of Stabiliser (based on weight of ester) | % Decomposition |
| --- | --- | --- |
| None | — | 6 |

| Stabiliser | % of Stabiliser (based on weight of ester) | % Decomposition |
|---|---|---|
| Epichlorohydrin | 5 | 4 |
| Aluminium tris(acetylacetonate) | 2 | 2 |

EXAMPLE 8

The procedure of Example 1 is repeated with the stabilisers listed below using diethyl-2-isopropyl-6-methylpyrimidin-4-yl phosphorothionate as the ester of thioacid of phosphorus, as a 10% solution in a commercially available mixture of alkyl benzenes, at a temperature of 80° C for 3 days.

| Stabiliser | % of Stabiliser (based on weight of ester) | % Decomposition |
|---|---|---|
| None | — | 14 |
| Epichlorohydrin | 5 | 4 |
| Aluminium tris(acetylacetonate) | 2 | 0 |

What we claim is:

1. A stabilized composition comprising an ester of an acid of thioacid of phosphorus which is normally unstable to storage when exposed to light, and a stabilizing amount of a chelate compound of aluminum, calcium, magnesium or zinc with a compound of the formula:

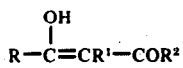

wherein R is a $C_{1-3}$ alkyl group, $R^1$ is a hydrogen atom and $R^2$ is a $C_{1-5}$ alkyl or alkoxy group, the amount of chelate compound being between 1 and 10% of the weight of ester.

2. A stabilized composition as claimed in claim 1 wherein the esterifying group is a heterocyclic hydroxylic compound.

3. A stabilized composition as claimed in claim 2 wherein the heterocyclic hydroxylic compound is a 4-hydroxypyrimidyl compound.

4. A stabilized composition as claimed in claim 1 wherein the ester is a phosphate.

5. A stabilized composition as claimed in claim 1 wherein the ester is an O,O-dialkyl phosphorus thionate.

6. A stabilized composition as claimed in claim 1, wherein the ester is a pesticide.

7. A stabilized composition as claimed in claim 1 wherein the compound of formula

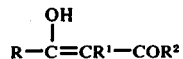

is acetyl acetone.

8. A stabilized composition as claimed in claim 1 wherein the chelate compound is of aluminum.

9. A stabilized composition as claimed in claim 1 which is a solution.

* * * * *